United States Patent
Govari et al.

(10) Patent No.: US 11,937,882 B2
(45) Date of Patent: Mar. 26, 2024

(54) ENT TOOLS

(71) Applicant: BIOSENSE WEBSTER (ISRAEL) LTD., Yokneam (IL)

(72) Inventors: Assaf Govari, Haifa (IL); Vadim Gliner, Haifa (IL); Yehuda Algawi, Binyamina (IL); Andres Claudio Altmann, Haifa (IL); Ilya Sitnitsky, Nahariya (IL)

(73) Assignee: Biosense Webster (Israel) Ltd., Yokneam (IL)

(*) Notice: Subject to any disclaimer, the term of this patent is extended or adjusted under 35 U.S.C. 154(b) by 720 days.

(21) Appl. No.: 16/943,805

(22) Filed: Jul. 30, 2020

(65) Prior Publication Data

US 2021/0059761 A1    Mar. 4, 2021

Related U.S. Application Data

(60) Provisional application No. 62/892,105, filed on Aug. 27, 2019.

(51) Int. Cl.
*A61B 34/20* (2016.01)
*A61B 1/00* (2006.01)
(Continued)

(52) U.S. Cl.
CPC ........ *A61B 34/20* (2016.02); *A61B 1/000094* (2022.02); *A61B 1/00097* (2022.02);
(Continued)

(58) Field of Classification Search
CPC ........... A61B 2018/00577; A61B 2018/00672; A61B 2018/00678; A61B 18/24; A61B 2034/2051; A61B 18/1492
See application file for complete search history.

(56) References Cited

U.S. PATENT DOCUMENTS

| | | | |
|---|---|---|---|
| 5,456,662 A | * | 10/1995 | Edwards ............ A61B 10/0233 604/22 |
| 5,556,377 A | * | 9/1996 | Rosen ...................... A61N 1/06 604/22 |

(Continued)

FOREIGN PATENT DOCUMENTS

WO    WO-9517132 A1 *  6/1995  ......... A61B 10/0233

OTHER PUBLICATIONS

International Search Report dated Jan. 18, 2021 from corresponding PCT Patent Application No. PCT/IB2020/057973.

*Primary Examiner* — Oommen Jacob

(57) ABSTRACT

A registration device, including a wand, a light guide passing through the wand, and a position sensor fixed to the wand. A light source outputs a modulated beam of light into a light guide proximal end, so that the light is emitted from a light guide distal end toward a surface in proximity to a wand distal tip. A detector receives, from the light guide proximal end, light reflected from the surface into the light guide distal end, and outputs a signal indicative of the reflected light intensity. A processor computes a distance from the distal tip of the wand to the surface by extracting a phase difference between the output beam and the reflected light from the signal, and computes a position of the surface in a sensor frame of reference responsively to the computed distance and the location of the distal tip found from the position sensor.

6 Claims, 8 Drawing Sheets

(51) Int. Cl.

| | | |
|---|---|---|
| *A61B 1/07* | (2006.01) | |
| *A61B 5/06* | (2006.01) | |
| *A61B 17/00* | (2006.01) | |
| *A61B 17/24* | (2006.01) | |
| *A61B 18/00* | (2006.01) | |
| *A61B 18/14* | (2006.01) | |
| *A61B 18/24* | (2006.01) | |
| *A61B 90/00* | (2016.01) | |

(52) U.S. Cl.
 CPC ............ *A61B 1/00194* (2022.02); *A61B 1/07* (2013.01); *A61B 5/066* (2013.01); *A61B 18/1492* (2013.01); *A61B 18/24* (2013.01); A61B 2017/00296 (2013.01); A61B 2017/00323 (2013.01); A61B 17/24 (2013.01); A61B 2018/00327 (2013.01); A61B 2018/00577 (2013.01); A61B 2018/00672 (2013.01); A61B 2018/00678 (2013.01); A61B 2018/00875 (2013.01); A61B 2034/2051 (2016.02); A61B 2034/2072 (2016.02); A61B 2090/3762 (2016.02)

(56) References Cited

U.S. PATENT DOCUMENTS

| | | | | |
|---|---|---|---|---|
| 5,718,702 A | * | 2/1998 | Edwards | A61B 18/18 606/41 |
| 5,735,847 A | * | 4/1998 | Gough | A61B 18/1477 606/41 |
| 5,824,005 A | * | 10/1998 | Motamedi | A61N 5/0601 600/374 |
| 7,883,536 B1 | * | 2/2011 | Bendett | A61N 5/0622 607/88 |
| 7,976,537 B2 | * | 7/2011 | Lieber | A61B 18/1492 606/41 |
| 8,048,063 B2 | * | 11/2011 | Aeby | A61B 5/6885 606/1 |
| 8,160,696 B2 | * | 4/2012 | Bendett | A61N 5/0601 607/3 |
| 2002/0077627 A1 | * | 6/2002 | Johnson | A61B 18/18 606/41 |
| 2003/0120270 A1 | * | 6/2003 | Acker | A61B 17/2202 606/41 |
| 2005/0101944 A1 | * | 5/2005 | Williams | A61B 18/22 606/41 |
| 2007/0083193 A1 | * | 4/2007 | Werneth | A61B 5/7445 606/41 |
| 2007/0270690 A1 | | 11/2007 | Woerlein | |
| 2008/0300588 A1 | * | 12/2008 | Groth | A61B 18/1206 606/34 |
| 2011/0009804 A1 | * | 1/2011 | Behnke | A61B 18/18 604/20 |
| 2011/0190760 A1 | * | 8/2011 | Niver | A61B 90/37 606/33 |
| 2012/0059364 A1 | * | 3/2012 | Baust | A61B 18/02 606/14 |
| 2014/0171936 A1 | * | 6/2014 | Govari | A61B 18/1492 606/34 |
| 2015/0359595 A1 | * | 12/2015 | Ben Oren | A61B 18/1492 606/41 |
| 2019/0069949 A1 | * | 3/2019 | Vrba | A61B 18/06 |
| 2021/0059761 A1 | * | 3/2021 | Govari | A61B 1/233 |

* cited by examiner

ENT TOOLS

CROSS-REFERENCE TO RELATED APPLICATIONS

This application claims the benefit of U.S. Provisional Patent Application 62/892,105 filed Aug. 27, 2019, which is incorporated herein by reference.

FIELD OF THE INVENTION

This invention relates generally to surgical tools, and specifically to tools which may be used for an ENT (ear, nose, and throat) investigation.

BACKGROUND OF THE INVENTION

In performing an ENT procedure, such as an investigation of the sinuses of a patient, it may be necessary for the operating physician to track the tools used for the procedure. While the tracking may be performed using fluoroscopy, fluoroscopy uses ionizing radiation which may harm both the patient and the physician.

Rather than using ionizing radiation, it is preferable to use a tracking system for the ENT tools that is free from such radiation. Such systems are well known in the art, and comprise, for example, a tracking system using magnetic and/or electric fields. However, in order that the tracking system provides results that are compatible with an image of the patient (such an image may be produced fluoroscopically or non-fluoroscopically) frames of reference of the tracking system and of the image need to be registered.

Methods for registration are known in the art. For example, if the patient image is a computerized tomography (CT) image, then voxels corresponding to the skin of the patient may be extracted from the CT image. Easily identifiable elements of the skin, such as a point between the eyes or the tip of the nose, may then be used for registration, by positioning a sensor operating in the tracking system on these points, and using the signals from the sensor for the registration.

SUMMARY OF THE INVENTION

An embodiment of the present invention provides a registration device, consisting of:

a wand having a distal tip;

a light guide passing through the wand and having a distal end at the distal tip of the wand and a proximal end extending proximally from the wand;

a position sensor fixed to the wand and configured to output a first signal indicative of a location of the distal tip in a sensor frame of reference;

a light source, which is coupled to output a beam of light, having an intensity that is modulated temporally at a predefined carrier frequency, into the proximal end of the light guide, whereby the light is emitted from the distal end of the light guide toward a surface in proximity to the distal tip of the wand;

a detector, configured to receive, from the proximal end of the light guide, the light that has been reflected from the surface into the distal end of the light guide, and to output a second signal that is indicative of the intensity of the reflected light; and a processor, configured to compute a distance from the distal tip of the wand to the surface by extracting a phase difference between the output beam and the reflected light from the second signal, and to compute a position of the surface in the sensor frame of reference responsively to the computed distance and the location of the distal tip that is indicated by the first signal.

In a disclosed embodiment there is a modulator coupled to the light source, that is configured to amplitude modulate the beam of light. Typically a frequency of amplitude modulation of the beam of light is set so that a separation between adjacent modulated peaks of the modulated light is between 1 cm and 4 cm.

In a further disclosed embodiment the first signal is indicative of an orientation of the distal tip in the sensor frame of reference.

In a yet further disclosed embodiment the processor is configured to determine a maximum and a minimum of the second signal in response to moving the wand distal tip in relation to the surface. The processor may be configured to acquire a given signal from the detector when the surface is at the distance from the wand distal tip, and to calculate the distance in response to the maximum, the minimum, and the given signal.

In an alternative embodiment the light source includes a laser that generates the light.

In a further alternative embodiment the processor is configured to determine the distance when the wand distal tip does not touch the surface.

In a yet further alternative embodiment the processor is configured to determine an initial value of the position of the surface, using the sensor, while touching the surface with the wand distal tip, and to update the initial value to a final value of the position, using the distance, while not touching the surface with the wand distal tip.

There is further provided, according to an embodiment of the present invention, apparatus, including:

a catheter consisting of an elongated member having a member distal end and an axis of symmetry, the member distal end being configured to be inserted into an orifice of a body of a living subject;

a first camera located on an outer surface of the member distal end and a second camera located on the outer surface of the member distal end, the cameras being oriented so that their respective fields of view are away from the axis of symmetry and include an overlapping portion; and a processor configured to acquire respective optical images from the cameras of tissue of the body in the overlapping portion, to identify common elements of the tissue in the respective optical images, to analyze a computerized tomography (CT) image of the body so as to identify the common elements in the CT image, and to overlay the respective optical images of the common elements on the common elements of the CT image so as to produce an enhanced CT image having the common elements.

In a disclosed embodiment the apparatus includes first and second magnetic sensors respectively located in the member distal end in proximity to the first and second cameras, and the processor is configured to acquire signals from the sensors so as determine a location of the member distal end in a frame of reference of the sensors, and to register the frame of reference of the sensors with a frame of reference of the CT image.

In a further disclosed embodiment the apparatus includes a wire fixed at a wire distal end to the member distal end, and pulling on the wire causes the member distal end to deflect from the axis of symmetry so as to alter the respective optical images acquired by the first and second cameras.

There is further provided, according to an embodiment of the present invention, apparatus, including:

a catheter consisting of an elongated member having a member distal end and an axis of symmetry, the member distal end being configured to be inserted into an orifice of a body of a living subject;

a motor fixed to a distal termination of the member distal end so that a motor shaft aligns with the axis of symmetry;

a revolvable base attached to the motor shaft;

a camera fixed to an outer surface of the revolvable base so that a field of view of the camera points away from the axis of symmetry; and a processor configured to rotate the camera on the motor shaft, to acquire a pair of optical images from the camera of tissue of the body as the camera rotates, to identify common elements of the tissue in the pair of optical images, to analyze a computerized tomography (CT) image of the body so as to identify the common elements in the CT image, and to overlay respective optical images of the common elements on the common elements of the CT image so as to produce an enhanced CT image including the common elements.

The processor may be configured to rotate the camera by oscillation about a selected direction, and to acquire the pair of optical images at respective ends of the oscillation.

There is further provided, according to an embodiment of the present invention, apparatus, including:

a catheter consisting of an elongated member having a member distal end and an axis of symmetry, the member distal end being configured to be inserted into an orifice of a body of a living subject;

a camera fixed to a distal termination of the member distal end so that a camera field of view aligns with the axis and faces away from the member distal end; and a biopsy needle attached to the member distal end so as to extend from the distal termination and oriented to be parallel to the axis of symmetry.

Typically, the apparatus includes a control attached to a proximal end of the elongated member, the control being coupled to the biopsy needle so that, on operation of the control, the biopsy needle retrieves a biopsy of tissue of the body. The tissue may be in the camera field of view prior to operation of the control.

There is further provided, according to an embodiment of the present invention, apparatus, including:

a catheter consisting of an elongated member having a member distal end and an axis of symmetry, the member distal end being configured to be inserted into an orifice of a body of a living subject;

a magnetic sensor located in the member distal end;

an electrode fixedly attached to, and enclosing a distal termination of the member distal end, the electrode being configured to convey radiofrequency (RF) energy to tissue of the body in contact with the electrode so as to ablate the tissue;

a fiber optic (FO) located on the axis of symmetry so that a FO distal end penetrates the electrode, the FO having an FO proximal end;

a laser coupled to the FO proximal end and being configured to input optical energy to the tissue, via the fiber optic, so as to ablate the tissue; and a processor coupled to actuate the laser and to supply RF energy to the electrode.

In a disclosed embodiment the processor is configured to actuate the laser when an impedance of the tissue is above a predetermined value.

In a further disclosed embodiment the processor is configured to supply the RF energy when an impedance of the tissue is below a predetermined value.

There is further provided, according to an embodiment of the present invention, a method, including:

providing a wand having a distal tip;

passing a light guide through the wand, the light guide having a distal end at the distal tip of the wand and a proximal end extending proximally from the wand;

fixing a position sensor to the wand, the sensor being configured to output a first signal indicative of a location of the distal tip in a sensor frame of reference;

coupling a light source to output a beam of light, having an intensity that is modulated temporally at a predefined carrier frequency, into the proximal end of the light guide, whereby the light is emitted from the distal end of the light guide toward a surface in proximity to the distal tip of the wand;

receiving with a detector, from the proximal end of the light guide, the light that has been reflected from the surface into the distal end of the light guide, and outputting a second signal that is indicative of the intensity of the reflected light; and computing a distance from the distal tip of the wand to the surface by extracting a phase difference between the output beam and the reflected light from the second signal, and computing a position of the surface in the sensor frame of reference responsively to the computed distance and the location of the distal tip that is indicated by the first signal.

There us further provided, according to an embodiment of the present invention, a method, including:

providing a catheter including an elongated member having a member distal end and an axis of symmetry, the member distal end being configured to be inserted into an orifice of a body of a living subject;

locating a first camera on an outer surface of the member distal end and locating a second camera on the outer surface of the member distal end, the cameras being oriented so that their respective fields of view are away from the axis of symmetry and include an overlapping portion;

acquiring respective optical images from the cameras of tissue of the body in the overlapping portion;

identifying common elements of the tissue in the respective optical images;

analyzing a computerized tomography (CT) image of the body so as to identify the common elements in the CT image; and overlaying the respective optical images of the common elements on the common elements of the CT image so as to produce an enhanced CT image comprising the common elements.

There is further provided, according to an embodiment of the present invention, a method, including:

providing a catheter consisting of an elongated member having a member distal end and an axis of symmetry, the member distal end being configured to be inserted into an orifice of a body of a living subject;

fixing a motor to a distal termination of the member distal end so that a motor shaft aligns with the axis of symmetry;

attaching a revolvable base to the motor shaft;

fixing a camera to an outer surface of the revolvable base so that a field of view of the camera points away from the axis of symmetry;

rotating the camera on the motor shaft;

acquiring a pair of optical images from the camera of tissue of the body as the camera rotates;

identifying common elements of the tissue in the pair of optical images;

analyzing a computerized tomography (CT) image of the body so as to identify the common elements in the CT image; and overlaying respective optical images of the common elements on the common elements of the CT image so as to produce an enhanced CT image comprising the common elements.

There is further provided a method, according to an embodiment of the present invention, including:

providing a catheter consisting of an elongated member having a member distal end and an axis of symmetry, the member distal end being configured to be inserted into an orifice of a body of a living subject;

fixing a camera to a distal termination of the member distal end so that a camera field of view aligns with the axis and faces away from the member distal end;

attaching a biopsy needle to the member distal end so as to extend from the distal termination; and orienting the needle to be parallel to the axis of symmetry.

There is further provided, according to an embodiment of the present invention, a method, including:

providing a catheter consisting of an elongated member having a member distal end and an axis of symmetry, the member distal end being configured to be inserted into an orifice of a body of a living subject;

locating a magnetic sensor in the member distal end;

fixedly attaching an electrode to a distal termination of the member distal end so as to enclose the distal end, the electrode being configured to convey radiofrequency (RF) energy to tissue of the body in contact with the electrode so as to ablate the tissue;

locating a fiber optic (FO) on the axis of symmetry so that a FO distal end penetrates the electrode;

coupling a laser to a FO proximal end, the laser being configured to input optical energy to the tissue, via the fiber optic, so as to ablate the tissue; and actuating the laser or supplying RF energy to the electrode.

The present disclosure will be more fully understood from the following detailed description of the embodiments thereof, taken together with the drawings, in which:

DETAILED DESCRIPTION OF EMBODIMENTS

Overview

Embodiments of the present invention provide a number of different tools that are configured for use in an ENT (ear, nose, and throat) procedure. During the procedure the tools are inserted into a patient, and are tracked within the patient using magnetic sensors respectively located in the different tools. Each magnetic sensor provides location and orientation for its respective tool, as measured in a frame of reference (FOR) defined by a magnetic field radiating system.

In order for the tracking to be correct, embodiments of the present invention register the magnetic field radiating system FOR with a previously acquired computerized tomography (CT) image FOR of the patient. In contrast to other registration systems, the registration system of the present invention does not rely on contact with the patient, and so errors (due, for example, to patient skin dimpling in contact systems) do not occur.

The non-contact registration system projects a coherent beam of light from a "wand" to the patient, and measures the distance of the wand to a region of the patient's skin interferometrically. The wand is also tracked in the magnetic system, so that the measured distances provide locations for the skin regions, as measured in the magnetic system FOR. A processor correlates the magnetic system FOR skin region locations with sections of an image of the skin derived from the CT image, and uses the correlation to register the two system FORs.

Embodiments of the invention also provide ENT catheters that are tracked in the registered magnetic system. The catheters comprise a catheter that is configured to generate three-dimensional images during the ENT procedure, a catheter that is configured to retrieve a biopsy of the patient, and a catheter configured to ablate patient tissue using either optical radiation or radiofrequency energy.

DETAILED DESCRIPTION

In the following, all directional references (e.g., upper, lower, upward, downward, left, right, top, bottom, above, below, vertical, and horizontal) are only used for identification purposes to aid the reader's understanding of the present invention, and do not create limitations, particularly as to the position, orientation, or use of embodiments of the invention.

Figure 1:
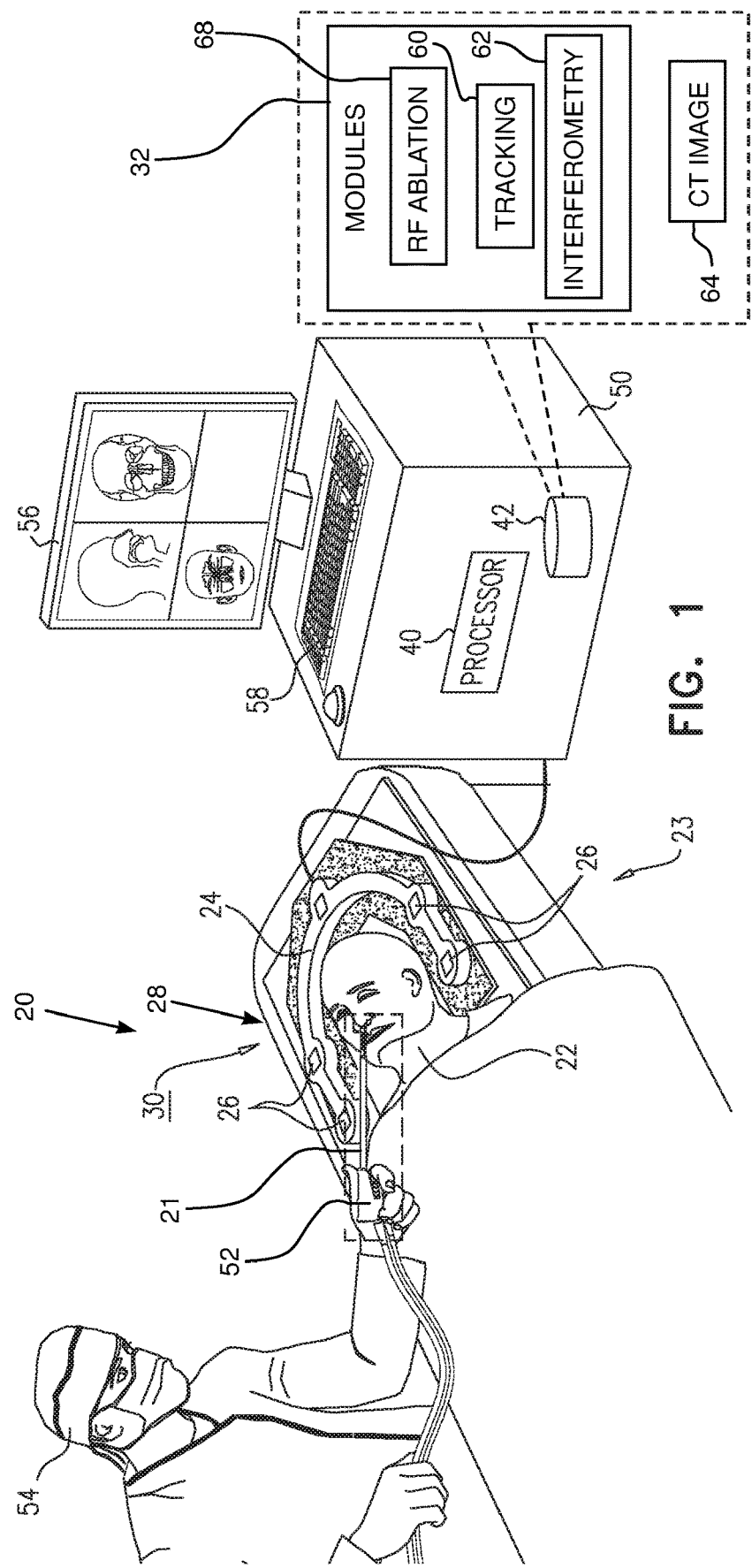
FIG. 1 is a schematic illustration of an ENT (ear, nose, and throat) system used for an ENT procedure, according to an embodiment of the present invention.

Reference is now made to FIG. 1, which is a schematic illustration of an ENT (ear, nose, and throat) system 20 used for an ENT procedure, according to an embodiment of the present invention. In the following description a physician 54 is assumed, by way of example, to use a number of tools during the procedure, for investigation of a patient 22. FIG. 1 illustrates a guide catheter 21 being used as one of the tools, and physician 54 may insert catheter 21 into patient 22 using a catheter handle 52. Handle 52 is also assumed to be used for the other tools described herein.

The operation and function of guide catheter 21 is described in more detail below, and the disclosure also describes the operation and function of the other tools used in the procedure. As is also described below, the location and orientation of a number of the tools are tracked using a magnetic tracking system 23.

Tracking system 23 comprises a magnetic radiator assembly 24 which is positioned beneath the patient's head. Assembly 24 comprises magnetic field radiators 26 which are fixed in position and which transmit alternating sinusoidal magnetic fields into a region 30 wherein the head of patient 22 is located. By way of example, radiators 26 of assembly 24 are arranged in an approximately horseshoe shape around the head of patient 22. Implementation of the present embodiment using other configurations of radiators 26 are also considered to be comprised within the scope of the present invention. The Carto® system produced by Biosense Webster, of 33 Technology Drive, Irvine, Calif. 92618 USA, uses a tracking system similar to that described herein for finding the location and orientation of a coil in a region irradiated by magnetic fields.

In order for tracking system 23 to track any particular tool, a magnetic position sensor 28A is incorporated into the tool. Sensor 28A is typically a triple axis sensor, formed of three coils oriented orthogonally to each other. In the following description, tools other than guide catheter 21 are described, and these tools may have magnetic sensors generally similar to sensor 28A, except where otherwise stated. Such sensors are labelled 28B, 28C, . . . , and are generically referred to herein as sensor 28. Elements of system 20, including radiators 26 of tracking system 23, are controlled by a system processor 40 and one or more modules described further below and stored in a memory 42.

Thus for tracking system 23 the processor and a tracking module 60 are also configured to receive the signals originating in the magnetic sensor 28 of a given tool, and to analyze and process the signals to derive location and orientation values for the sensor, and thus for the tool, in a frame of reference defined by radiator assembly 24. Processor 40 may be mounted in a console 50, which comprises operating controls 58 that typically include a keypad and/or a pointing device such as a mouse or trackball. Console 50 connects to radiators 26 via a cable and/or wirelessly. Physician 54 uses operating controls 58 to interact with the processor while performing the procedures described herein using system 20. While performing the procedures, the processor may present results of the procedures on a screen 56.

Processor 40 uses software stored in memory 42 to operate system 20. The software may be downloaded to processor 40 in electronic form, over a network, for example, or it may, alternatively or additionally, be provided and/or stored on non-transitory tangible media, such as magnetic, optical, or electronic memory.

Tracking module 60 is stored in a software module bank in memory 42. Bank 32 also comprises an interferometry module 62 and a radiofrequency ablation module 68. Tracking module 60 communicates with processor 40 so as to provide the functionality described above for assembly 24. The functions of the other modules in bank 32 are explained in detail below.

In addition, memory 42 stores a computerized tomography (CT) image 64 of patient 22. CT image 64 is herein assumed to be produced by fluoroscopy.

As stated above, in the procedure described herein the ENT tools used in the procedure are tracked using tracking system 23. In order for the tracking to be accurate, a frame of reference of system 23, also referred to herein as the frame of reference of assembly 24, is registered with a frame of reference of CT image 64, and such registration is typically performed prior to insertion of the ENT tool into patient 22. A method for registration is described hereinbelow.

Registration of Magnetic Tracking System 23 with CT Image 64

Figure 2A:
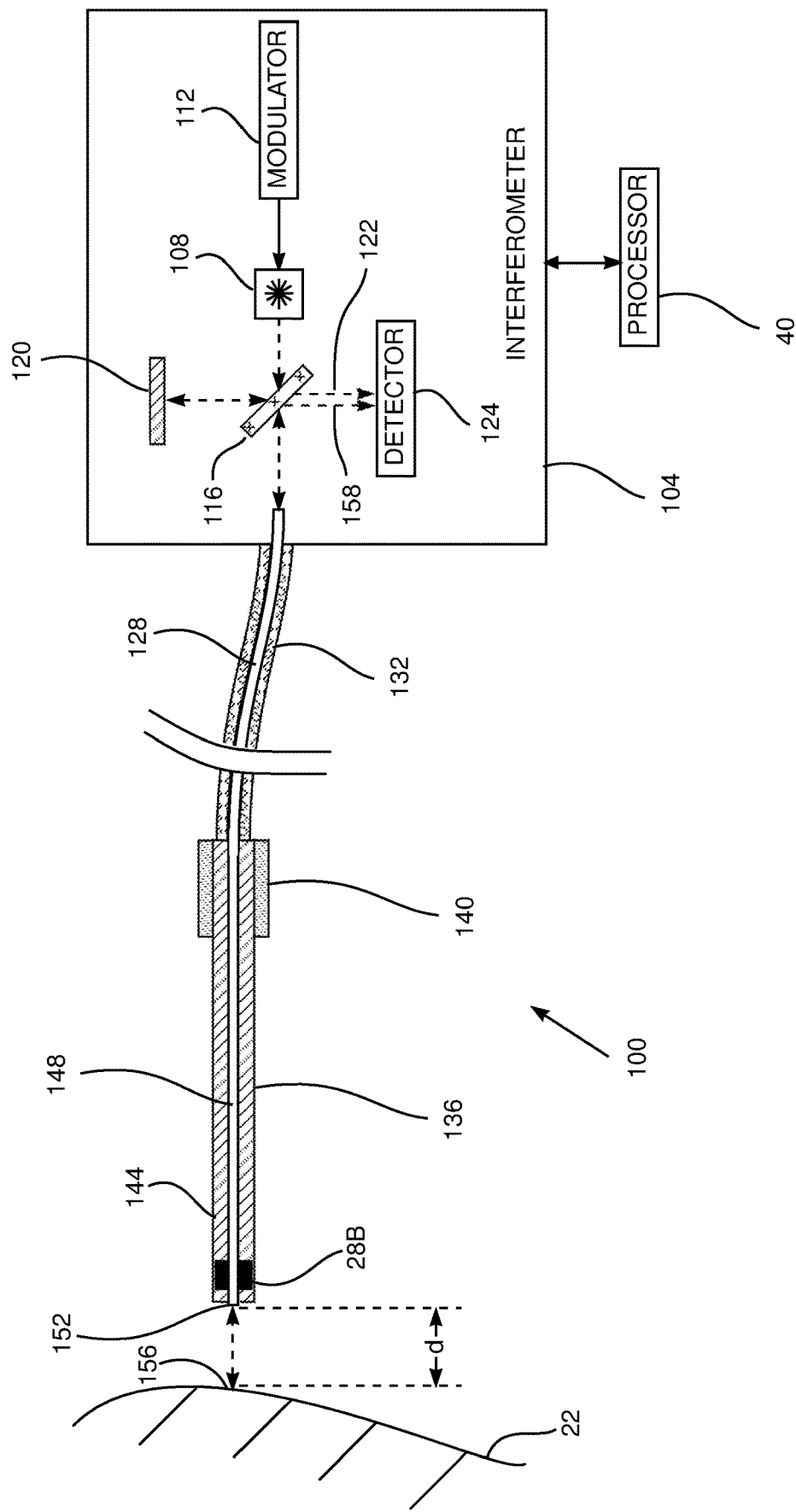
FIG. 2A is a schematic illustration of an interferometry system used in registering a tracking system with a computerized tomography image.
Figure 2B:
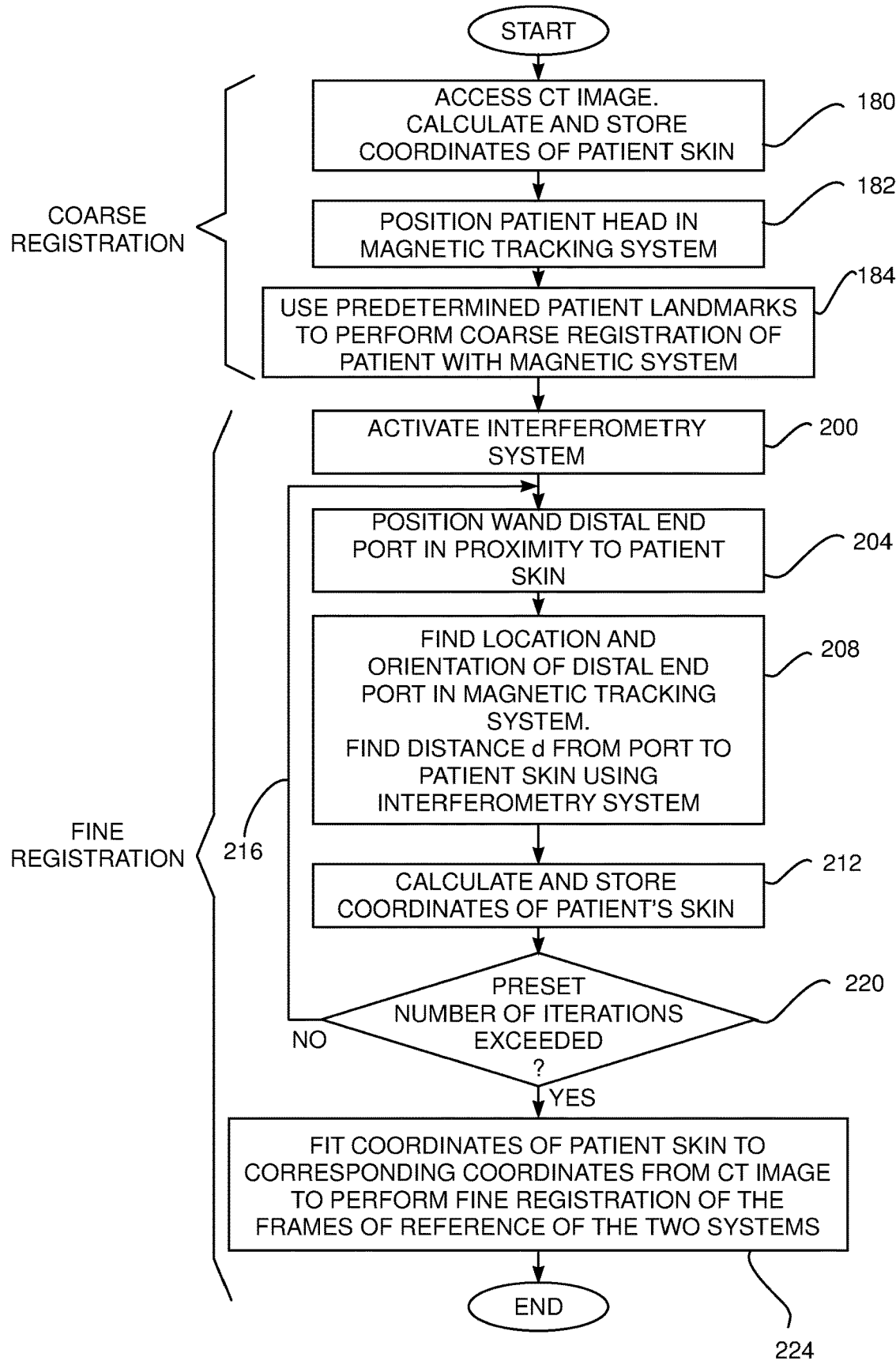
FIG. 2B is a flowchart of steps used for the registration, according to an embodiment of the present invention.

FIG. 2A is a schematic illustration of an interferometry system 100 used in registering tracking system 23 with CT image 64, and FIG. 2B is a flowchart of steps used for the registration, according to an embodiment of the present inventions. As is described in more detail below, system 100 is used for a process of fine registration of the tracking system with the CT image, after an initial process of coarse registration of the system with the image has been performed.

System 100 comprises a coherent light interferometer 104, typically located in console 50, the elements of the interferometer being controlled by processor 40. For clarity and simplicity, focusing elements, such as lenses and/or mirrors, used for the operation of interferometer 104 are not shown in the figure.

Interferometer 104 comprises a light source 108, herein by way of example assumed to be a laser, and referred to as laser 108, which is selected to transmit a beam of light in a visible or near-visible region of the electromagnetic spectrum. In one embodiment laser 108 transmits at approximately 600 nm. Laser 108 is temporally amplitude modulated by a modulator 112, and the frequency of the amplitude modulation is set so that in one embodiment the distance between adjacent modulated peaks of the laser light output in air from laser 108 is approximately 1 cm. To achieve a separation of 1 cm the modulation is at approximately 30 GHz. Other embodiments of the invention have a separation between adjacent modulated peaks that is up to approximately 4 cm, so that modulator 112 may be operated at frequencies between approximately 7.5 GHz and approximately 30 GHz. In the following description, the distance between adjacent modulated peaks is represented by the symbol λ, and λ is assumed to be 2 cm.

Other methods for modulation of laser 108, such as using an external modulator placed in the laser beam emitted by laser 108 (in place of modulator 112) are also considered to be comprised within the scope of the present invention The amplitude modulated light from laser 108 is transmitted to a semi-reflecting mirror 116, so that approximately 50% of the light transmits through the mirror and approximately 50% reflects from the mirror. The reflected light is conveyed to a mirror 120, which returns the light to semi-reflecting mirror 116. Approximately 50% of the returned light transmits through the semi-reflecting mirror as a first detector beam 122 to a light detector 124.

The transmitted light from semi-reflecting mirror 116 is conveyed to the entrance port, i.e., the proximal end, of a fiber optic (FO) light guide 128. FO guide 128 exits from interferometer 104, and in the portion external to the interferometer is encased in a flexible protective sheath 132.

At their distal end, sheath 132 and FO 128 are attached to the proximal end of an inflexible wand 136, and during operation of interferometry system 100, physician 54 holds wand 136 by a wand handle 140. Wand 136 comprises a wand case 144 within which is a FO light guide 148 that is optically coupled, at its proximal end, to the distal end of FO light guide 128, so that the two light guides act as one light guide. FO 148 terminates, at a distal end port 152 of the fiber optic, at the distal end or tip of wand 136.

Also incorporated into the distal tip of wand 136 is a magnetic sensor 28B, which is typically configured as described above for sensor 28A. The function of sensor 28B, within tracking system 23, is described in more detail below.

When system 100 is operative, amplitude modulated light from semi-reflecting mirror 116 is transmitted via FO 128 and FO 148 and exits from distal end port 152. The direction of the exiting light corresponds to the direction of FO 148, and thus to the orientation of wand 136. Consequently, the direction of the light exiting from port 152 may be found from signals acquired by sensor 28B.

The exiting light strikes a surface 156 of patient 22, and a portion reflects back to port 152, and from the port to semi-reflecting mirror 116. Mirror 116 reflects approximately 50% of the light received from port 152 as a second detector beam 158 to detector 124.

Detector beams 122 and 158 interfere at detector 124, and the interference may be constructive, destructive, or an intermediate type of interference between constructive and destructive. The actual interference depends on the different path lengths followed by the two beams, from their origination at mirror 116 to their termination at detector 124, since the different path lengths introduce a phase difference $\phi$ between the beams.

The path length followed by beam 158, from its origination on mirror 116, includes a forward and a reverse traverse between distal end port 152 and surface 156, and the distance between these two points is herein termed "d."

It will be understood that the phase difference $\phi$ and distance d are related, so that as long as d≤0.5λ we may write equation (1):

$$d = f(\phi) \quad (1)$$

where f is a monotonic function relating $\phi$ and d.

A signal S generated at the detector, and provided to processor 40, is a maximum $S_{max}$ for constructive interference when $\phi=0$, is a minimum $S_{min}$ for destructive interference when $\phi=\pi$, and is between the minimum and the maximum, herein termed $S_b$, for an intermediate type of interference when $0<\phi<\pi$.

If $S_{max}$, $S_{min}$, and $S_b$ are all known, the value of $\phi$ applicable for the generation of $S_b$ can be calculated, using equation (2):

$$\phi = g(S_{max}, S_{min}, S_b) \quad (2)$$

where g is a function.

Substituting equation (2) into equation (1) gives:

$$d = h(S_{max}, S_{min}, S_b) \quad (3)$$

where h is the function f×g.

The numerical relationship, corresponding to function h, between the variables of equation (3) may be determined by calibration. In the calibration, wand 136 is positioned so that distal end port 152 is at measured distances from a reflecting surface. Processor 40 records values of distances and the detector signals, including $S_{max}$, $S_{min}$, and $S_b$.

The flowchart of FIG. 2B describes how system 100 is used to evaluate distance d.

FIG. 2B is a flowchart of steps used in registering the frame of reference of magnetic tracking system 23 with the frame of reference of CT image 64. As stated above, the registration consists of an initial coarse registration process, followed by a fine registration process. The fine registration uses interferometry system 100.

In an initial step 180 of the coarse registration process, processor 40 accesses CT image 94, and calculates and stores three-dimensional (3D) coordinates of the skin the patient 22.

In a positioning step 182, the head of patient 22 is positioned above magnetic radiator assembly 24, and tracking system 23 is activated. The activation enables processor 40 to track the location and orientation of sensor 28B. At this stage of the procedure, the activation of system 23 does not require that interferometry system 100 is activated.

In a coarse registration step 184, the physician touches the distal end of wand 136 on predetermined landmarks of the patient's head. The landmarks are typically easily identifiable regions, such as the nose tip, a region between the eyes, the center of the patient's forehead, and regions on either side of the eyes. As each landmark is touched, the physician uses controls 58 to have the processor record the signals from sensor 28B, and to analyze the recorded signals to provide the location (in the frame of reference of tracking system 23) of the touched landmark. The processor then stores the locations of the respective landmarks in memory 42.

Step 184 is repeated for a preset number of different landmarks, for example four landmarks.

Once the preset number of landmarks have been touched, and their respective locations recorded and stored, processor 40 correlates the 3D skin coordinates of the patient, found in step 180, with the stored landmark locations. The correlation is to find a best fit between the two sets of data, and typically uses an algorithm such as the iterative closest point (ICP) algorithm to find the best fit. The correlation found provides a coarse registration between CT image 64 and magnetic tracking system 23, so that step 184 concludes the coarse registration process.

The coarse registration provided by steps 108-184 is somewhat inaccurate because the requirement to touch the patient typically leads to depression of the skin at the position touched. There is also inaccuracy because of the relatively few numbers of landmarks used for the correlation. The following fine registration process corrects for both of these inaccuracies.

In an initial step 200 of the fine registration process, interferometry system 100 is activated. The activation includes calibrating the system so as to determine function $h(S_{max}, S_{min}, S_b)$ of equation (3). It will be understood that the calibration may be performed by positioning targets at known distances d, d≤0.5λ, from port 152, while using processor 40 to record signals $S_b$ acquired by detector 124.

In an operation step 204, physician 54 holds wand 136 by its handle, and positions the wand so that the light exiting distal end port 152 strikes a section of the skin of the head of patient 22. In the description hereinbelow, except where otherwise stated, the section of the skin is assumed to be surface 156.

The physician positions the wand so that distal end port 152 does not touch the skin of the patient. Rather the physician moves the wand so that the distal end port is within 0.5λ from the skin.

Prior to moving the port to be within 0.5λ from the skin the physician moves the wand backwards and forwards relative to the patients skin so that processor 40 captures values of signals $S_{max}$ and $S_{min}$ acquired by detector 124. The description below explains how system 100 checks that these movements have been correctly made.

In a signal acquisition step 208, processor 40 records signals from detector 124, and checks that the signals have passed through a maximum value and a minimum value. When the signals have passed these values, the processor stores them as $S_{max}$ and $S_{min}$, and may then provide a notice to the physician on screen 56 to move the distal end port close to the patient's skin.

Also in signal acquisition step 208, once values of $S_{max}$ and $S_{min}$ have been stored, processor 40 and tracking module 60 acquire signals generated in sensor 28B, and analyze the signals to find a location $(x_d, y_d, z_d)$ of distal end port 152. The processor and the module also use the signals to calculate an orientation of the port. It will be understood that the values of the location and orientation of the port are for the frame of reference of assembly 24.

The processor, using the coarse registration found in step 184, checks if location $(x_d, y_d, z_d)$ is less than or equal to $0.5\lambda$ from the skin of patient 22. If location $(x_d, y_d, z_d)$ is more than $0.5\lambda$ from the skin of the patient, the physician may be requested to move port 152 closer to the patient, typically by providing a notice on screen 56.

When location $(x_d, y_d, z_d)$ is less than or equal to $0.5\lambda$ from the skin of the patient, the processor, together with interferometry module 62, acquires the signal $S_b$ generated in detector 124. The processor uses acquired signal $S_b$ and stored signals $S_{max}$ and $S_{min}$ in equation (3) to determine a value for distance d.

In a processing step 212, processor 40 uses the value of d, the location $(x_d, y_d, z_d)$ of port 152, and the orientation of the port, to calculate three-dimensional coordinates $(x_p, y_p, z_p)$ of surface 156. The processor stores the calculated value of $(x_p, y_p, z_p)$ in memory 42. As for location $(x_d, y_d, z_d)$, location $(x_p, y_p, z_p)$ is in the frame of reference of assembly 24.

As shown by an arrow 216 steps 204-212 are iterated a preset number of times, for example 10 times, and at each iteration physician 54 holds the wand so that the light exiting distal end port 152 strikes a different section of the skin of the head of patient 22. At each iteration the physician holds the wand so that port 152 does not touch the skin of the patient, while ensuring (as is described above) that the distance from the distal end port to the patient's skin is less than or equal to $0.5\lambda$.

In a condition step 220, processor 40 checks if the preset number of iterations has been exceeded. If it has not, then the iterations continue. If step 200 returns positive, then control continues to a registration step 224.

In a final fine registration step 224, processor 40 compares the different stored values of $(x_p, y_p, z_p)$ with three-dimensional values of the skin of patient 22, derived from CT image 64 (as described in more detail below), in order to find a best fit between the two sets of values. Processor 40 typically performs the comparison using the same algorithm as used for the coarse registration, such as the iterative closest point (ICP) algorithm, but any other convenient algorithm providing a best fit may be used. The fit determined in step 224 provides translation and/or rotation vectors registering the frame of reference of the magnetic tracking system with the frame of reference of the CT image.

Implementation of the present embodiment using other methods for processor 40 to register the two frames of reference, including variations on the steps described in the flowchart of FIG. 2B, are also considered to be comprised within the scope of the present invention. For example, rather than performing a preset number of iterations of steps 204-212, processor 40 may perform registration step 224 after each pass through steps 204-212, and iterate steps 204-212 until the fit calculated in step 224 is equal to or better than a predetermined threshold.

Typically, once processor 40 has registered the two frames of reference, an indication of successful registration, such as displaying a notice on screen 56, may be provided to physician 54.

The frames of reference registration system described hereinabove correlates three-dimensional coordinates of a patient's skin that are measured in two modalities—a magnetic tracking system and a fluoroscopic CT imaging system. However, in contrast to other methods registering these two modalities by finding coordinates of a patient's skin, interferometry system 100 measures the coordinates in a non-contact manner, so obviating errors that arise in methods using contact with the patient's skin. Furthermore, also in contrast to other methods that may be used for measuring patient skin coordinates, the resolution of interferometry system 100 may be adjusted, by adjusting the modulation frequency of modulator 112. Consequently, the resolution of system 100 may be adjusted according to the resolution of CT image 64, so as to provide an optimal best fit in step 224.

The registration described above may be used in tracking tools, described below, used in the ENT procedure referred to herein.

Guide Catheter 21

Figure 3A:
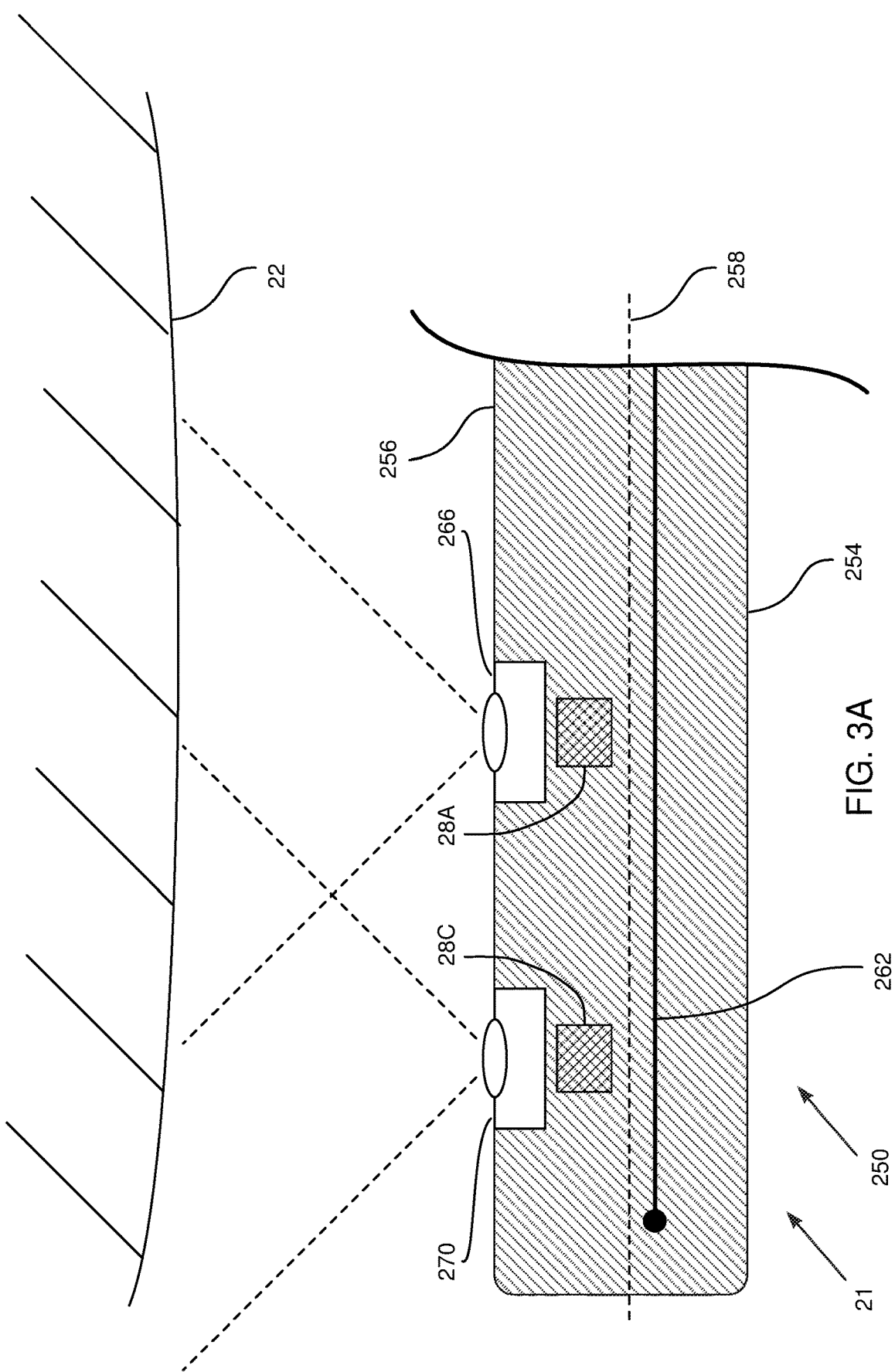
FIG. 3A is a schematic diagram illustrating a distal end of a guide catheter.
Figure 3B:
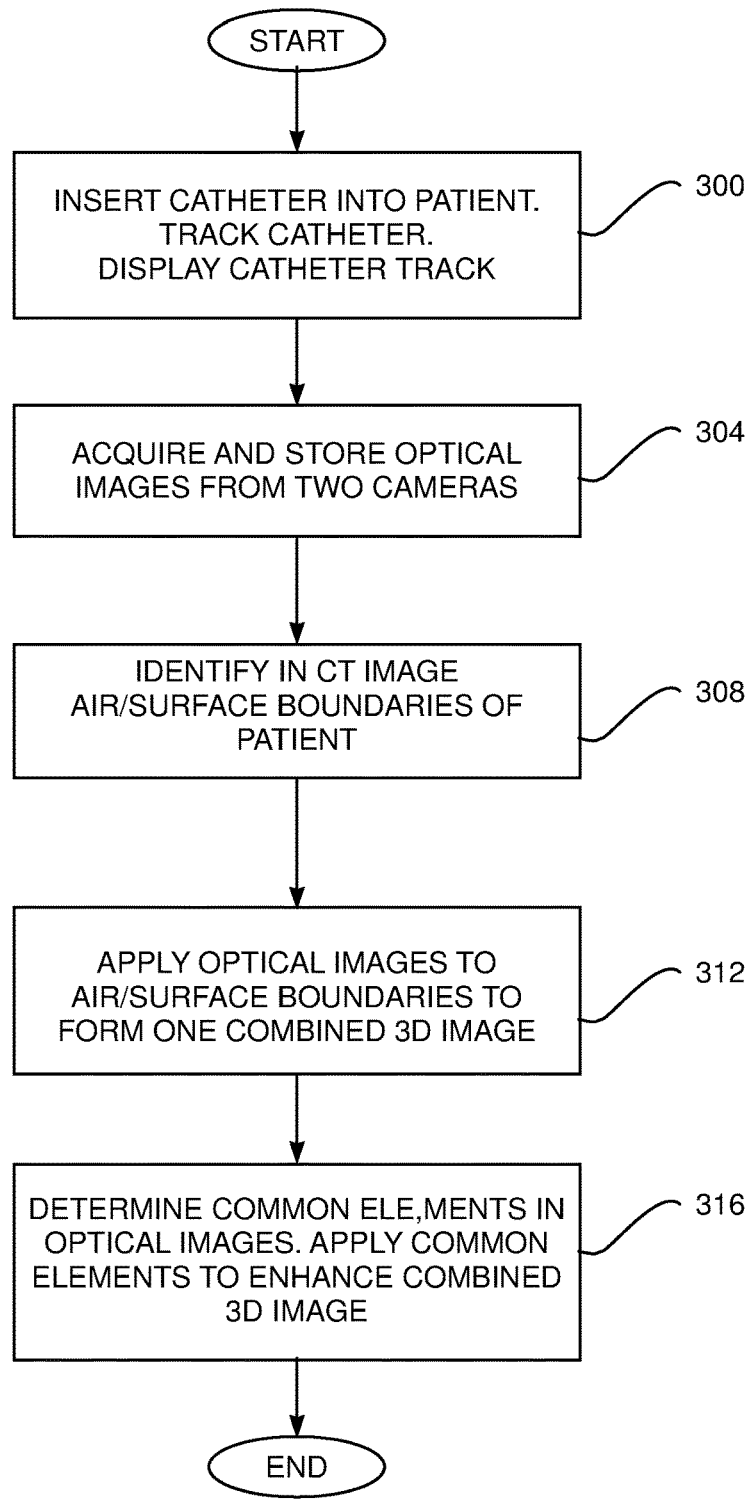
FIG. 3B is a flowchart of steps followed in using the catheter, according to an embodiment of the present invention.

FIG. 3A is a schematic diagram illustrating a distal end 250 of guide catheter 21, and FIG. 3B is a flowchart of steps followed in using the catheter, according to an embodiment of the present invention. Physician 54 uses catheter 21 to provide an image of internal elements of patient 22. As is explained below, the images formed by the catheter may be used in the presentation of an enhanced image of the internal elements of the patient to physician 54.

While the following description of distal end 250 assumes that the distal end is flexible, changes to the description, mutatis mutandis, will be apparent if the distal end is inflexible, so that the scope of the present invention comprises flexible and inflexible distal ends for catheter 21.

Distal end 250 is formed from a biocompatible plastic such as a polyamide, and in one embodiment the distal end comprises a cylindrical tube 254 with a diameter of approximately 2 mm. Tube 254 is normally straight, having an axis of symmetry 258. However, the tube may be bent from the axis by physician 54 pulling on a proximal end of a wire 262, the wire being attached at its distal end to a distal portion of tube 254. Physician 54 typically pulls wire 262 using a control on handle 52 (FIG. 1) and tube 254 may be returned to its straight configuration if the physician ceases pulling, also using the control.

Fixedly attached to an outer surface 256 of tube 254 are two substantially similar cameras 266, 270, which are typically separated by a preset distance. In one embodiment the preset distance is 10 mm, but other embodiments typically have the preset distance in a range from approximately 3 mm to approximately 30 mm. The two cameras are located on the surface of tube 254 so that a line segment joining the cameras is parallel to axis of symmetry 258, and the cameras are oriented so that their fields of view are away from the axis of symmetry. Furthermore, as is illustrated in the figure, there is a portion of the fields of view where the fields overlap, the overlapping depending upon the size of the fields of view and on the distance from the cameras. In one embodiment, the field of view of each of the cameras is 90°, and the overlap begins at a distance of 5 mm from the cameras.

Magnetic sensors 28A, 28C are fixedly attached to tube 254 and are respectively located in proximity to cameras 266, 270. Processor 40 uses the signals from the magnetic sensors, typically after a process of calibration, to provide location and orientation values for each of the cameras.

As stated above physician 54 uses catheter 21 in an ENT procedure, so that distal end 250 may be in air and cameras 266, 270 are able to acquire images of internal elements of patient 22, such as the patient's sinuses. While during the procedure the cameras may be obstructed by mucus or blood, embodiments of the present invention typically comprise methods for cleaning the cameras, such as providing irrigation to the camera lenses. For simplicity, irrigation channels that may be present in distal end 250 are not shown in FIG. 3A.

FIG. 3B is a flowchart of steps followed in using catheter 21. In an initial step 300, after registration as described above, physician 54 inserts the catheter into a nasal aperture of patient 22, and processor 40 and tracking module 60 track distal end 250, using signals from sensors 28A, 28C. The tracking is typically presented as an overlay on CT image 64 presented on screen 56.

In an image acquisition step 304, at a position selected by the physician (which may be at the initial insertion or later), cameras 266, 270 are activated, and the processor stores optical images acquired by the cameras in memory 42. The acquired optical images are of elements of patient 22 occurring at an air/solid interface of the patient, i.e. at the outer skin of the patient and/or at an internal patient surface such as the surface of the patient sinuses. Such elements can also be identified by processor 40 in CT image 64 because of changes in Hounsfield Unit (HU) values at the interface.

In an image identification step 308, using the fact that the HU value for air is −1000, processor 40 identifies in image 64 boundaries from air to a surface of patient 22, since the surface, such as the skin of the patient, has an HU value substantially different from −1000. (The method for identification described herein may also be used in registration step 224 described above.)

In an initial 3D image process step 312, since the locations and orientations of cameras 266, 270 with respect to the elements being imaged are known from their respective sensor signals, by virtue of the frames of reference registration that has been performed, processor 40 applies the images acquired in step 304 to the boundaries identified in step 308. The application typically uses projective texture mapping to overlay the images acquired in step 304 on the boundaries, producing two 3D images (because of the two different fields of view). The processor typically displays the two 3D images as one combined 3D image on screen 56.

In an enhanced 3D image process step 316, processor 40 determines common elements in the two optical images formed by cameras 266, 270, corresponding to the region wherein the two fields of view overlap. The determination may be made by image analysis, although any other convenient method for common element determination may be used. Once the common elements have been determined, processor 40 may apply the common elements to enhance the combined 3D image formed in step 312. The enhancement improves the three-dimensional representation on screen 56, for instance by allowing the physician to rotate the combined image so that different aspects of the common elements, that are not visible in only one image, become visible.

As is described above, catheter 21 produces enhanced 3D images using two images formed by separate cameras in distal end 250 of the catheter. Alternatively or additionally, physician 54 may use a rotating catheter 400, described below with reference to FIGS. 4A and 4B, to produce enhanced 3D images.

Rotating Catheter 400

Figure 4A:
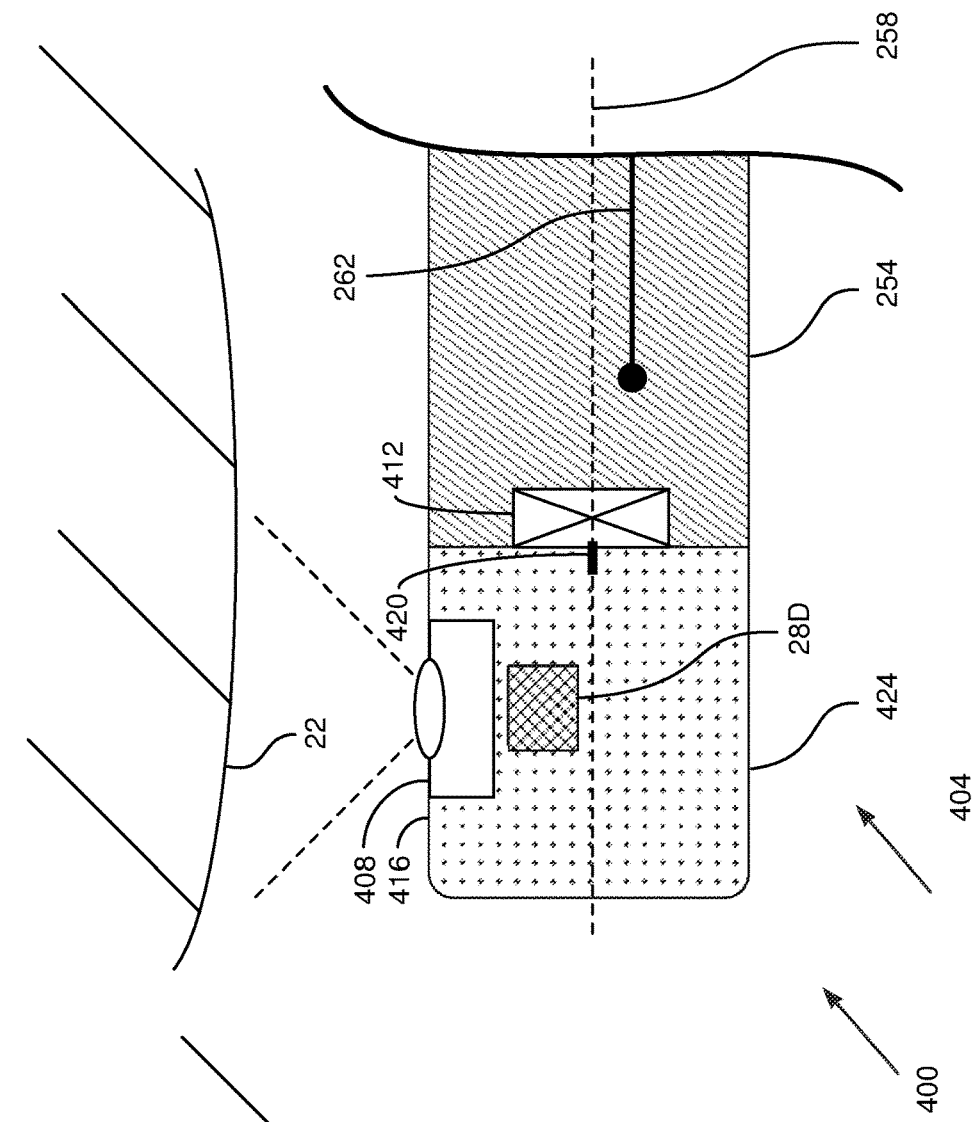
FIG. 4A is a schematic cross-section of a distal end of a catheter.
Figure 4B:
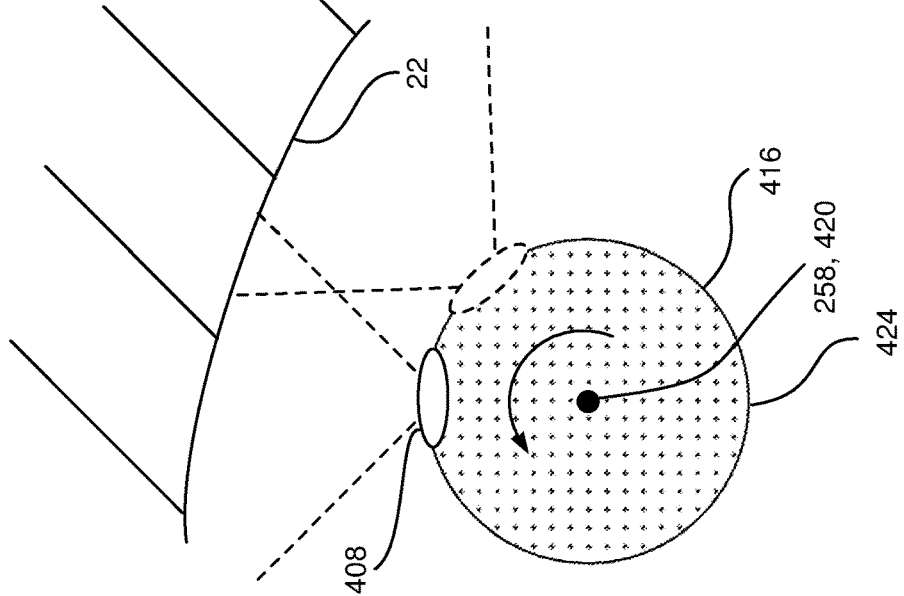
FIG. 4B is a schematic view of the catheter along an axis of symmetry of the catheter, according to an embodiment of the present invention.

FIG. 4A is a schematic cross-section of a distal end 404 of catheter 400, and FIG. 4B is a schematic view of the catheter along an axis of symmetry of the catheter, according to an embodiment of the present invention. Apart from the differences described below, the operation of distal end 404 is generally similar to that of distal end 250 (FIGS. 3A and 3B), and elements indicated by the same reference numerals in both distal ends are generally similar in construction and in operation. Thus, as for distal end 250, distal end 404 is configured to acquire multiple optical images of elements of an identifiable section of patient 22, and these multiple images are processed substantially as described above in the flowchart of FIG. 3B.

However, in contrast to distal end 250, distal end 404 comprises only one camera 408, substantially similar to cameras 266, 270. Furthermore, camera 408 is not fixedly attached to surface 256 of distal end 404. Rather, a motor 412 is fixed to the distal termination of tube 254 and a revolvable cylindrical base 416 is attached by a shaft 420, lying along axis 258, to the motor. Base 416 has a diameter substantially the same as that of tube 254.

Camera 408 is fixedly attached to an outer surface 424 of base 416, and is oriented so that its field of view is away from axis 258. A magnetic sensor 28D is fixedly attached to base 416 in proximity to camera 408. As for catheter 21, processor 40 uses the signals from the sensor 28D, typically after a process of calibration, to provide location and orientation values for camera 408.

On insertion by physician 54 of catheter 400 into patient 22, camera 408 is able to acquire optical images of the internal surfaces of patient 22. In order to acquire the types of images that provide an enhanced 3D image, similar to the images acquired by distal end 254, physician 54 activates motor 412 to rotate base 416.

While base 416 rotates, camera 408 acquires images, and FIG. 4B illustrates schematically the camera acquiring two such images. During the base rotation, processor 40 uses signals from sensor 28D to determine, at each point of image acquisition, the location and orientation of camera 408.

In one embodiment motor 412 rotates base 416 so that in one revolution camera 408 acquires 180 images. In this case the orientation of the camera between adjacent images differs by 2°. In an alternative embodiment, prior to motor 412 rotating base 416, physician 54 observes the image generated by camera 408, and selects a direction for the images to be generated. On selection, motor 412 oscillates base 416 about the selected direction, by an angle selected by physician 54, for example ±30°, and camera 408 acquires images at the endpoints of the oscillation.

Processor 40 uses the pairs of adjacent images acquired by rotation of base 416, substantially as described in the steps of the flowchart of FIG. 3B, to produce 3D images and enhanced 3D images of patient 22 that are displayed on screen 56 to the physician.

Typically, once physician 54 has viewed the images generated by catheter 21 and/or catheter 400, the physician may continue with the procedure using a biopsy catheter 500 and an ablation catheter 600. Biopsy catheter 500 and ablation catheter 600 are described below.

Biopsy Catheter 500

Figure 5:
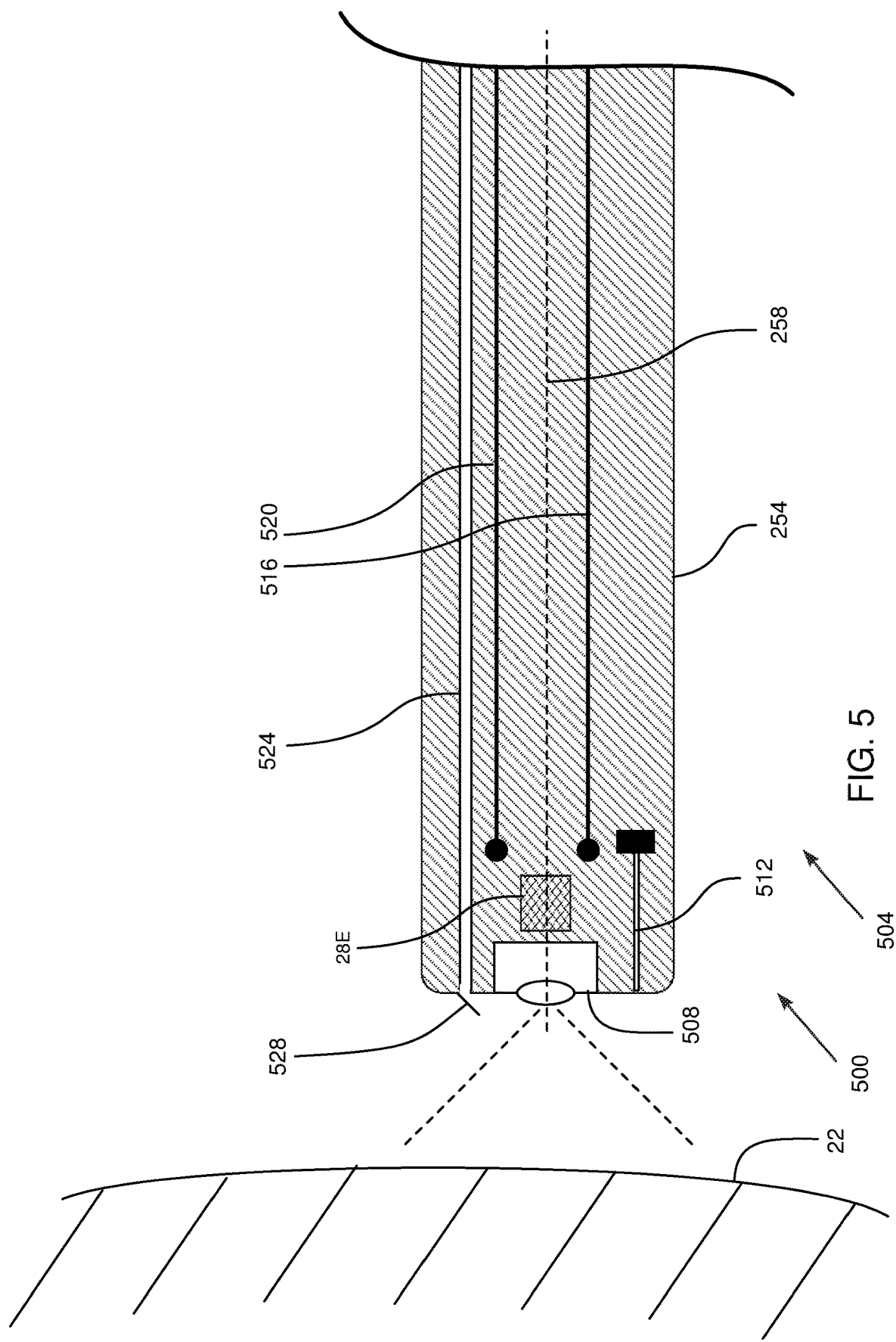
FIG. 5 is a schematic cross-section of a distal end of a biopsy catheter, according to an embodiment of the present invention.

FIG. 5 is a schematic cross-section of a distal end 504 of biopsy catheter 500, according to an embodiment of the present invention. Apart from the differences described below, the structure of distal end 504 is generally similar to that of distal end 250 (FIG. 3A), and elements indicated by the same reference numerals in both distal ends are generally similar in construction and in operation.

Distal end 504 is used to acquire a biopsy of a portion of patient 22 selected by physician 54. Thus, in contrast to distal end 250, distal end 504 comprises one camera 508 that is fixedly attached to the termination of the distal end so that its field of view aligns with axis 258 and faces away from the distal end. The camera is used to view, and enable the physician to select, a section of patient 22 from where a biopsy is to be retrieved. A magnetic sensor 28E is fixedly connected to the distal end, in proximity to camera 508. The sensor provides the physician with location and orientation information for the camera, and also enables processor 40 to display the location and orientation information of the distal end as an overlay on CT Image 64 on screen 56

The distal end also comprises a biopsy needle 512, attached so as to extend from the termination of the distal end, and oriented to be parallel with axis 258. Operation of needle 512 is typically via controls in handle 52 attached to leads to the needle, but for simplicity such leads are not shown in the figure. Once needle 512 has been used to perform the biopsy, catheter 500 may be removed from patient 22 for retrieval of the biopsy.

By way of example, distal end 504 comprises two wires 516, 520, generally similar in function and structure to wire 262, which are attached at their distal ends to a distal portion of tube 254. In other embodiments more than two wires are attached to the distal portion of tube 254. Using controls for the wires in handle 52, the physician is able to deflect tube in multiple directions from axis 258, so facilitating more exact positioning of needle 512 prior to performing the biopsy.

Distal end 504 also comprises an irrigation channel 524, which is configured to transfer irrigation fluid, typically saline solution. The fluid, typically operated by a control in handle 52, may be deflected by a deflector 528, attached to the termination of tube 254, so that the deflected fluid traverses and cleans the lens of camera 508.

Ablation Catheter 600

Figure 6:
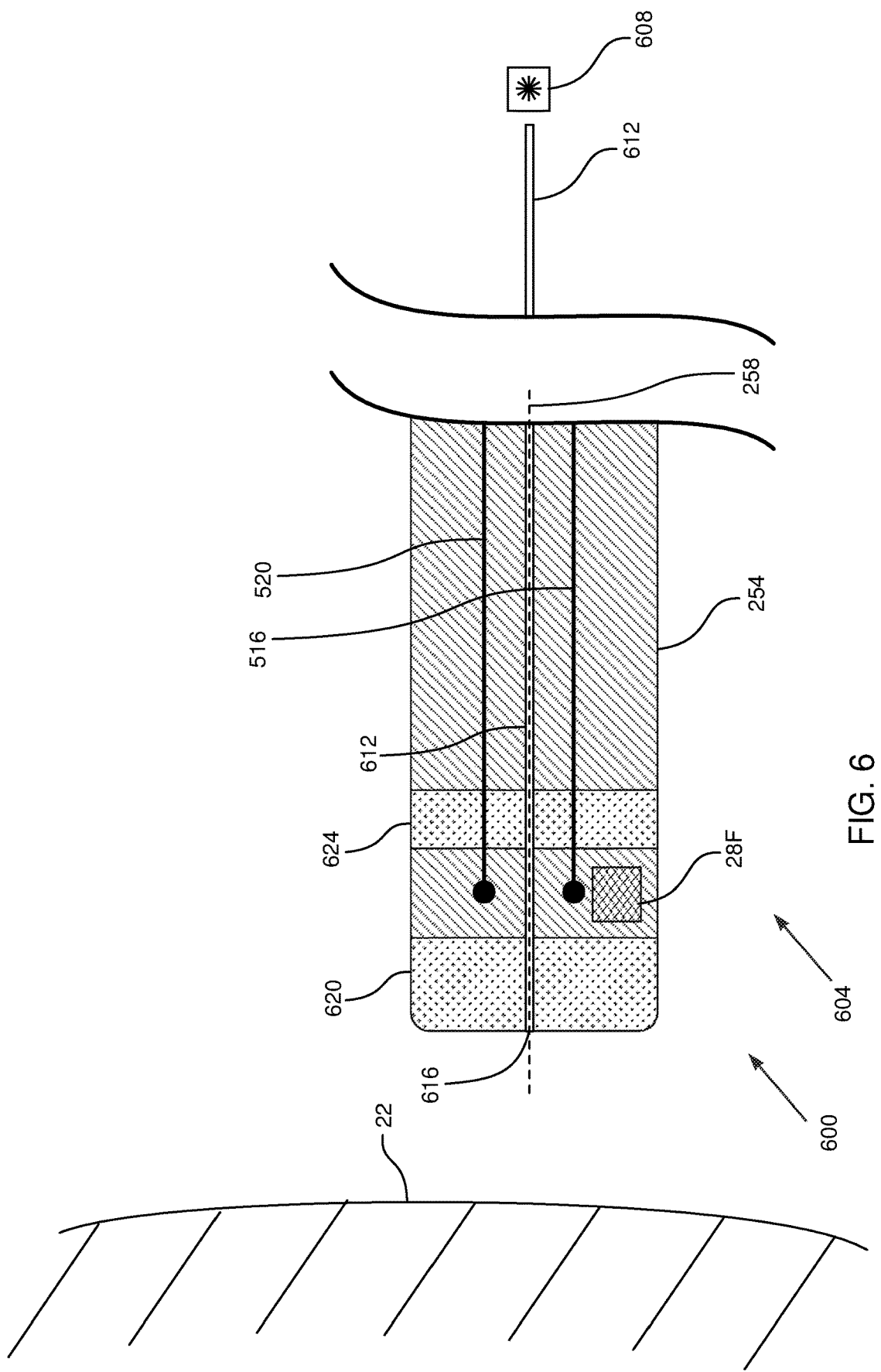
FIG. 6 is a schematic cross-section of a distal end of an ablation catheter, according to an embodiment of the present invention.

FIG. 6 is a schematic cross-section of a distal end 604 of ablation catheter 600, according to an embodiment of the present invention. Apart from the differences described below, the structure of distal end 604 is generally similar to that of distal end 250 (FIG. 3A), and elements indicated by the same reference numerals in both distal ends are generally similar in construction and in operation.

Distal end 604 is used to ablate a portion of patient 22 selected by physician 54, using either optical radiation or radiofrequency (RF) energy, and in contrast to distal end 250, distal end 604 typically does not comprise a camera. In order to navigate distal end 604, the distal end comprises a magnetic sensor 28F fixedly attached to tube 254. Processor 40 uses signals from the sensor to calculate the location and orientation of the distal end, and these may be used in an image (typically an overlay on CT image 64) tracking the distal end that is displayed on screen 56.

Distal end 604 comprises a fiber optic (FO) 612 that typically is aligned along axis 258, and that is coupled, at a proximal end of the FO, to a laser 608. In one embodiment laser 608 comprises a Nd:YAG laser. Laser 608 is typically mounted in console 50, and controls to operate the laser may be situated in handle 52 and/or the console.

When operated, laser 608 directs optical power into FO 612, so that power exiting from a distal end 616 of the fiber optic is sufficient to ablate a section of patient 22 upon which the power impinges.

Distal end 604 also comprises an electrode 620, herein assumed to be a cup-shaped electrode fixedly attached to the termination of the distal end. Electrode 620 is configured to convey RF energy, generated by processor 40 and ablation module 68 (FIG. 1) to tissue of patient 22 that is in contact with the electrode.

It will be understood that physician 54 is able to use catheter 600 for either RF ablation of tissue, or for optical radiation ablation of the tissue. The mode selected may depend on the impedance of the tissue; for example, if the tissue is bone, having a high impedance, RF ablation may be inefficient, and in this case the physician may select to ablate using laser 608. Conversely, if the tissue is fat, having a relatively low impedance, it may be more efficient to use RF ablation.

Distal end 604 typically comprises one or more other electrodes 624, which may be used for signal acquisition and/or for pacing. Typically, when not being used for ablation, electrode 620 may also be used for signal acquisition and/or for pacing.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus, comprising:
 a catheter comprising an elongated member having a member distal end and an axis of symmetry, the member distal end being configured to be inserted into an orifice of a body of a living subject;
 a magnetic sensor located in the member distal end;
 cup-shaped electrode fixedly attached to and capping a termination of the member distal end, the electrode being configured to convey radiofrequency (RF) energy to tissue of the body in contact with the electrode so as to ablate the tissue, wherein the cup-shaped electrode includes a base portion and a cylindrical wall portion surrounding the base portion;
 a fiber optic (FO) extended along the axis of symmetry so that a FO distal end penetrates the electrode through the base portion, the FO having an FO proximal end;
 a laser coupled to the FO proximal end and being configured to input optical energy to the tissue, via the fiber optic, so as to ablate the tissue; and
 a processor coupled to actuate the laser and to supply RF energy to the electrode.

2. The apparatus according to claim 1, wherein the processor is configured to actuate the laser when an impedance of the tissue is above a predetermined value.

3. The apparatus according to claim 1, wherein the processor is configured to supply the RF energy when an impedance of the tissue is below a predetermined value.

4. A method, comprising:
 providing a catheter comprising an elongated member having a member distal end and an axis of symmetry, the member distal end being configured to be inserted into an orifice of a body of a living subject;
 locating a magnetic sensor in the member distal end;
 fixedly attaching a cup-shaped electrode that caps a distal termination of the member distal end, the electrode being configured to convey radiofrequency (RF) energy to tissue of the body in contact with the electrode so as to ablate the tissue, wherein the cup-shaped electrode includes a base portion and a cylindrical wall portion surrounding the base portion;
 extending a fiber optic (FO) along the axis of symmetry so that a FO distal end penetrates the electrode;

coupling a laser to a FO proximal end, the laser being configured to input optical energy to the tissue, via the fiber optic, so as to ablate the tissue; and actuating the laser or supplying RF energy to the electrode.

5. The method according to claim 4, and comprising actuating the laser when an impedance of the tissue is above a predetermined value.

6. The method according to claim 4, and comprising supplying the RF energy when an impedance of the tissue is below a predetermined value.

* * * * *